(12) United States Patent
Baert et al.

(10) Patent No.: US 6,342,245 B1
(45) Date of Patent: Jan. 29, 2002

(54) COMPOSITIONS OF LIPID LOWERING AGENTS

(75) Inventors: Lieven Baert, Brugge; Geert Verreck, Malle, both of (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/530,170

(22) PCT Filed: Oct. 27, 1998

(86) PCT No.: PCT/EP98/06998

§ 371 Date: Apr. 24, 2000

§ 102(e) Date: Apr. 24, 2000

(87) PCT Pub. No.: WO99/22738

PCT Pub. Date: May 14, 1999

(30) Foreign Application Priority Data

Nov. 3, 1997 (EP) ............................................ 97203407

(51) Int. Cl.[7] ................................................ A61K 9/48
(52) U.S. Cl. ........................ 424/451; 424/464; 424/463; 424/489; 424/494; 424/493; 424/496; 424/497; 424/465; 424/474; 424/470; 514/252; 548/127; 548/129; 548/182; 548/213; 548/225; 548/228; 548/229; 548/263.2; 548/144; 548/251; 548/255; 548/311.1

(58) Field of Search .......................... 514/252; 544/285, 544/364, 367, 369, 370; 548/127, 129, 182, 213, 225, 228, 229, 263.2, 144, 251, 255, 311.1; 424/494, 489, 480, 501, 451, 464, 474, 465, 490

(56) References Cited

U.S. PATENT DOCUMENTS 5,521,186 A * 5/1996 Heeres et al. ................ 514/252
5,929,075 A * 7/1999 Heeres et al. ................ 514/252

FOREIGN PATENT DOCUMENTS

WO    WO 96/13499    5/1996

* cited by examiner

*Primary Examiner*—Thurman K. Page
*Assistant Examiner*—Liliana Di Nola-Baron

(57) ABSTRACT

The present invention is concerned with novel pharmaceutical compositions of lipid lowering agents which can be administered to a mammal suffering from hyperlipidemia, obesitas or atherosclerosis, whereby a single such dosage form can be administered once daily, and in addition at any time of the day independently of the food taken in by said mammal. These novel compositions comprise particles obtainable by melt-extruding a mixture comprising a lipid lowering agent and an appropriate water-soluble polymer and subsequently milling said melt-extruded mixture.

32 Claims, No Drawings

COMPOSITIONS OF LIPID LOWERING AGENTS

CROSS REFERENCE TO RELATED APPLICATIONS

This application is the national stage of PCT/EP98/06998, filed Oct. 27, 1998, which application claims priority from EP 97203407.8, filed Nov. 3, 1997.

The present invention is concerned with novel pharmaceutical compositions of lipid lowering agents which can be administered to a mammal suffering from hyperlipidemia, obesitas or atherosclerosis whereby a single such dosage form can be administered once daily. These novel compositions comprise innovative particles obtainable by melt-extruding a mixture comprising a lipid lowering agent and an appropriate water-soluble polymer and subsequently milling said melt-extruded mixture.

The present invention provides particles of lipid lowering agents previously disclosed in WO-96/13499 that have the formula

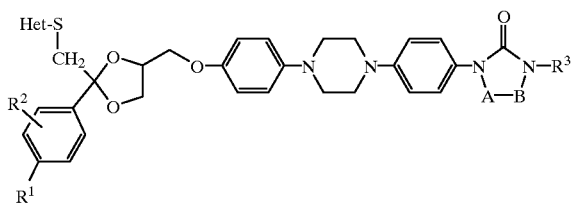

(I)

the N-oxides, one or more stereochemically isomeric forms, and the pharmaceutically acceptable acid addition salts thereof, wherein A and B taken together form a bivalent radical of formula:

—N=CH— (a),
—CH=N— (b),
—CH$_2$—CH$_2$— (c),
—CH=CH— (d),
—C(=O)—CH$_2$— (e),
—CH$_2$—C(=O)— (f), wherein in the bivalent radicals of formula (a) and (b) the hydrogen atom may be replaced by $C_{1-6}$alkyl; and wherein in the bivalent radicals of formula (c), (d), (e), (f), one or two hydrogen atoms may be replaced by $C_{1-6}$alkyl;

$R^1$ is hydrogen, $C_{1-6}$alkyl or halo;
$R^2$ is hydrogen or halo;
$R^3$ is hydrogen; $C_{1-8}$alkyl; $C_{3-6}$cycloalkyl; or $C_{1-8}$alkyl substituted with hydroxy, oxo, $C_{3-6}$cycloalkyl or aryl;
Het is a heterocycle selected from the group consisting of pyridine; pyridine substituted with one or two substituents selected from $C_{1-6}$alkyl, hydroxy, $C_{1-6}$alkyloxy, trihalomethyl, amino, mono- or di($C_{1-6}$alkyl)amino or aryl; pyrimidine; pyrimidine substituted with one or two substituents selected from $C_{1-6}$alkyl, hydroxy, $C_{1-6}$alkyloxy, trihalomethyl, amino, mono- or di($C_{1-6}$alkyl)-amino or aryl; tetrazole; tetrazole substituted with $C_{1-6}$alkyl or aryl; triazole; triazole substituted with one or two substituents selected from $C_{1-6}$alkyl, hydroxy, $C_{1-6}$alkyloxy, trihalomethyl, amino, mono- or di($C_{1-6}$alkyl)-amino; thiadiazole; thiadiazole substituted with one or two substituents selected from $C_{1-6}$alkyl, hydroxy, $C_{1-6}$alkyloxy, trihalomethyl, amino, mono- or di($C_{1-6}$alkyl)amino; oxadiazole substituted with one or two substituents selected from $C_{1-6}$alkyl, hydroxy, $C_{1-6}$alkyloxy, trihalomethyl, amino, mono- or di($C_{1-6}$alkyl)amino; imidazole; imidazole substituted with one or two substituents selected from $C_{1-6}$alkyl, hydroxy, $C_{1-6}$alkyloxy, trihalomethyl, amino, mono- or di($C_{1-6}$alkyl)amino; thiazole; thiazole substituted with one or two substituents selected from $C_{1-6}$alkyl, hydroxy, $C_{1-6}$alkyloxy, trihalomethyl, amino, mono- or di($C_{1-6}$alkyl)amino; oxazole; oxazole substituted with one or two substituents selected from $C_{1-6}$alkyl, hydroxy, $C_{1-6}$alkyloxy, trihalomethyl, amino, mono- or di($C_{1-6}$alkyl)amino; and aryl is phenyl or phenyl substituted with $C_{1-6}$alkyl or halo.

The compounds of formula (I) and their salts have a very limited aqueous solubility and hardly dissolve when in crystalline form. In order to ensure that the compounds of formula (I) have sufficient bioavailability, they may be dissolved in water in the presence of solubilizing agent such as a cyclodextrin derivative e.g. 2-hydroxypropyl-beta-cyclodextrin. The present invention provides an alternative dosage form that does not require the use of a solubilizing agent and still has sufficient bioavailability.

In the compounds of formula (I) defined hereinbefore, the heterocyclic radical "Het" is bound to the sulfur atom via a carbon atom.

As used in the foregoing definitions halo is generic to fluoro, chloro, bromo and iodo; $C_{1-6}$alkyl defines straight and branched chain saturated hydrocarbon radicals having from 1 to 6 carbon atoms such as, for example, methyl, ethyl, propyl, butyl, pentyl, hexyl, 1-methylethyl, 2-methylpropyl and the like; $C_{1-8}$alkyl defines $C_{1-6}$alkyl and the higher homologues thereof containing 7 or 8 carbon atoms such as, for example, heptyl or octyl and the branched isomers thereof. $C_{3-6}$cycloalkyl defines saturated cyclic hydrocarbon radicals having from 3 to 6 carbon atoms, such as cyclopropyl, cyclobutyl, cyclopentyl, or cyclohexyl.

Het may in particular be a radical of formula

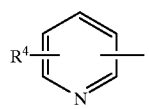

(a)

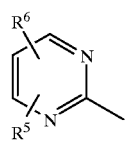

(b)

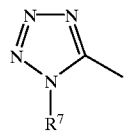

(c)

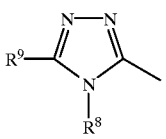
(d)

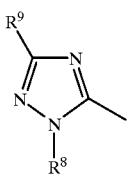
(e)

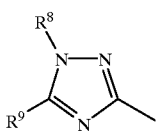
(f)

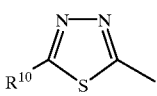
(g)

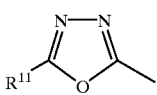
(h)

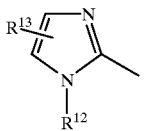
(i)

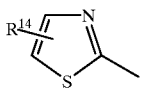
(j)

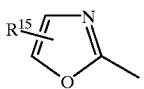
(k)

wherein:
$R^4$ is hydrogen or $C_{1-6}$alkyl;
$R^5$ and $R^6$ are hydrogen, $C_{1-6}$alkyl or amino;
$R^7$ is hydrogen or $C_{1-6}$alkyl;
each $R^8$ independently is hydrogen or $C_{1-6}$alkyl;
each $R^9$ independently is hydrogen, $C_{1-6}$alkyl, trifluoromethyl, amino or hydroxy;
$R^{12}$ is hydrogen or $C_{1-6}$ alkyl
$R^{10}$ and $R^{11}$ each independently are hydrogen or $C_{1-6}$alkyl;
$R^{13}$ is hydrogen or $C_{1-6}$alkyl;
$R^{14}$ is hydrogen, $C_{1-6}$alkyl or hydroxy;
$R^{15}$ is hydrogen or $C_{1-6}$alkyl.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which the compounds of formula (I) as well as the salts thereof, are able to form. Such solvates are for example hydrates, alcoholates and the like. Conversely the salt form can be converted by treatment with alkali into the free base form.

The term "stereochemically isomeric forms" as used hereinbefore defines all the possible stereoisomeric forms in which the compounds of formula (I) may exist, thus, also including all enantiomers, enantiomeric mixtures and diastereomeric mixtures. Unless otherwise mentioned or indicated, the chemical designation of compounds denotes the mixture of all possible stereochemically isomeric forms, said mixtures containing all diastereomers and enantiomers of the basic molecular structure. The same applies to the intermediates as described herein, used to prepare endproducts of formula (I).

Pure enantiomeric forms of the compounds of formula (I) are defined as enantiomers substantially free of other enantiomeric or diastereomeric forms of the same basic molecular structure of said compounds.

Asymmetric centers have ether the R- or the S-configuration. The terms cis and trans are used herein in accordance with Chemical Abstracts nomenclature and refer to the position of the substituents on a ring moiety, more in particular on the dioxolane ring in the compounds of formula (I). In the latter instance, when establishing the cis or trans configuration, the substituent with the highest priority on the carbon atom in the 2 position of the dioxolane ring, and the substituent with the highest priority on the carbon atom in the 4 position of the dioxolane ring are considered (the priority of a substituent being determined according to the Cahn-Ingold-Prelog sequence rules). When said two substituents with highest priority are at the same side of the ring then the configuration is designated cis, if not, the configuration is designated trans.

The compounds of formula (I) wherein the stereogenic carbon atom in the 2-position of the dioxolane moiety has the S-configuration are particularly preferred.

The compounds of formula (I) may also exist in their tautomeric forms. For instance, heterocycles such as, for example, pyridine, pyrimidine, triazole, thiadiazole, oxadiazole, imidazole, thiazole and oxazole, which are substituted with hydroxy, amino or $C_{1-6}$alkylamino may exist in their tautomeric form. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperazine-nitrogens are N-oxidized.

Interesting compounds are those compounds of formula (I) wherein $R^1$ is chloro or fluoro, especially chloro.

Further interesting compounds are those compounds of formula (I) wherein $R^1$ is $C_{1-6}$alkyl, especially methyl.

Other interesting compounds are those compounds of formula (I) wherein $R^2$ is hydrogen, chloro or fluoro, preferably hydrogen.

Yet another group of interesting compounds of formula (I) are those compounds wherein the bivalent radical —A—B— is —CH=CH—, —N=CH— or —CH=N—, especially —CH=N— or —N=CH—. In said bivalent radicals, the hydrogen atom may be replaced by $C_{1-6}$alkyl, especially methyl.

A group of particular compounds comprises those compounds wherein $R^3$ is $C_{1-8}$alkyl or $C_{3-6}$cycloalkyl, preferably butyl, pentyl or cyclopentyl.

A group of preferred compounds of formula (I) comprises those compounds wherein Het is a triazole, substituted triazole, imidazole, substituted imidazole, thiazole, or substituted thiazole.

More preferred compounds of formula (I) are those interesting or particular compounds wherein Het is 2-thiazolyl, 4-methyl-4H-1,2,4-triazol-3-yl, 4H-1,2,4-triazol-3-yl, 2-methyl-2H-1,2,4-triazol-3-yl or 2H-1,2,4-triazol-3-yl.

The most preferred compounds are:

cis-4-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-2-(1-methylpropyl)-3H-1,2,4-triazol-3-one; more in particular the diastereoisomer (-)-[2S-[2alpha, 4alpha(S*)]] compound 40 in table 3, which is referred to as Compound A hereinafter;

cis-2-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-4-(1-methylpropyl)-3H-1,2,4-triazol-3-one;

cis-2-[4-[4-[4-[[2-(4-fluorophenyl)-2-[[(4-methyl-4H-,1,2,4-triazol-3-yl)thio]methyl]-1,3-dioxolan-4-yl]methoxy]phenyl]-1-piperazinyl]phenyl]-4-cyclopentyl-2,4-dihydro-3H-1,2,4-triazol-3-one;

cis-2-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4dihydro-4-pentyl-3H-1,2,4-triazol-3-one;

cis-4-(1-ethylpropyl)-2-[4-[4-[4-[[2-(4-fluorophenyl)-2-[[(4-methyl-4H-1,2,4,-triazol-3-yl)thio]methyl]-1,3-dioxolan-4-yl]methoxy]phenyl]-1-piperazinyl]phenyl]-2,4dihydro-3H-1,2,4-triazol-3-one;

a pharmaceutically acceptable acid addition salt or a stereochemically isomeric form thereof.

In view of their apolipoprotein B inhibiting activity and concomitant lipid lowering activity, the present compounds are useful as a medicine especially in a method of treating patients suffering from hyperlipidemia, obesitas or atherosclerosis. In particular the present compounds may be used for the manufacture of a medicine for treating disorders caused by an excess of very low density lipoproteins (VLDL) or low density lipoproteins (LDL), and especially disorders caused by the cholesterol associated with said VLDL and LDL.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylomicronaemai syndrome, familial hypertriglyceridaemia. The present compounds may also be used to prevent or treat patients suffering from obesitas or from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

The dosage depends on the particular compound of formula (I) used and its formulation, the particular condition being treated and the severity thereof, the age, weight and general physical condition of the patient and whether the patient is fasting or is fed, as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereunder are therefore guidelines only. Those of skill in the treatment of hyperlipidemia, obesitas or atherosclerosis can determine an effective daily amount of Compound A from the test results presented hereinafter. In general, a therapeutically effective dose will range from 0.01 mg/kg to 5 mg/kg body weight, more preferably from 0.1 mg/kg to 3 mg/kg body weight. It suffices to administer a single dose once daily orally. Said once daily dose is preferably formulated as a unit dosage form, for example, containing 50 mg to 250 mg, and in particular 100 to 150 mg of Compound A per unit dosage form.

As already mentioned, the compounds of formula (I) and their salts have a very limited aqueous solubility and hardly dissolve when in crystalline form. They may be dissolved in water in the presence of a solubilizing agent such as cyclodextrin derivative. It is highly desirable, however, to have solid pharmaceutical dosage forms of the compounds of formula (I) besides liquid formulations. Dosage forms with a high drug content, one unit of which contains the required daily dose of the active ingredient instead of two or more such units, are another desirable goal in the pharmaceutical development. Ideally, the bioavailability of dosage forms should be independent of food taken in or fasting by the patient in order that the medicament can be administered to the patient—or for that matter, to any mammal—at any time of the day, in particular that it can be administered to patients (mammals) in a fasted state. The present invention provides a once daily (o.d.) solid dosage form of a compound of formula (I) that has nearly equal bioavailability in fasted and in fed volunteers.

At this stage, it may be remarked that therapeutically effective plasma levels of the lipid lowering agent or active metabolites thereof are maintained easily for at least 24 hours. The main condition is that the lipid lowering agent must reach the plasma. The absorption of dissolved lipid lowering agent from the stomach is in itself not a problem. Thus, there is no need for a sustained release dosage form of compound of formula (I), an immediate release form will do just as well. In other words, the main problem with the administration of a lipid lowering agents in therapeutically effective amounts is in the first place concerned with ensuring that a sufficient amount of lipid lowering agent remains in solution sufficiently long enough to allow it to get into the circulation, and that it does not convert into a form that is not readily bioavailable, in particular into crystalline lipid lowering agent (which forms, for example, when lipid lowering agent precipitates in an aqueous medium).

The present invention provides pharmaceutical compositions of lipid lowering agents and a water-soluble polymer which can be administered to a mammal, in particular a human, suffering from hyperlipidemia, obesitas or atherosclerosis whereby a single such dosage form can be administered once daily. The bioavailability of the drug from these dosage forms in fasted and in fed mammals is comparable. The dosage forms can be prepared easily, for example by conventional tabletting or capsule filling techniques. The dosage forms comprise a therapeutically effective amount of particles as described in detail hereunder.

Said novel particles consist of a solid dispersion comprising (a) a lipid lowering agent of formula (I), or a stereoisomer or a mixture of two or more stereoisomers thereof, and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion will be called "a solid solution" hereinafter. Solid solutions are preferred physical systems because the components therein are usually readily bioavailable to the organisms to which they are administered. This advantage can probably be explained by the ease with which said solid solutions can form liquid solutions when contacted with a liquid medium such as gastric juice. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to particles having domains or small regions wherein amorphous, microcrystalline or crystalline (a), or amorphous, microcrystalline or crystalline (b), or both, are dispersed more or less evenly in another phase comprising (b), or (a), or a solid solution comprising (a) and (b). Said domains are regions within the particles distinctively marked by some physical feature, small in size compared to the size of the particle as a whole, and evenly and randomly distributed throughout the particle. Domains of (a) typically have a size of up to about 25 $\mu$m, preferably up to 20 $\mu$m.

The particles according to the present invention can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

The melt-extrusion process comprises the following steps:

a) mixing the components (a) and (b), b) optionally blending additives with the thus obtained mixture, c) heating and kneading the blend in a compounder to a homogenous melt, d) forcing the thus obtained melt through one or more nozzles; and e) cooling the melt till it solidifies.

The terms "melt" and "melting" should be interpreted broadly. For our purposes, these terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

One of the most important parameters of melt extrusion is the temperature at which the melt-extruder is operating. It was found that the operating temperature can easily range between about 120° C. and about 300° C., and preferably ranges between about 170° C. and about 230° C., in particular between 180° C. and 220° C. At temperatures lower than 120° C., lipid lowering agents will not dissolve completely in most water-soluble polymers and the extrudate will not have the required bioavailability. In addition, the process is difficult because of the high viscosity of the mixture. At temperatures of more than 300° C. the water-soluble polymer may decompose to an unacceptable level. It may be noted that there is little need to fear decomposition of the lipid lowering agents at temperatures up to 300° C. since most of these active ingredients are thermally very stable.

The throughput rate is of importance because even at relatively low temperatures the water-soluble polymer may start to decompose when it remains too long in contact with the heating element.

It will be appreciated that the person skilled in the art will be able to optimize the parameters of the melt extrusion process within the above given ranges. The working temperatures will also be determined by the kind of extruder or the kind of configuration within the extruder that is used. Most of the energy needed to melt, mix and dissolve the components in the extruder can be provided by the heating elements. However, the friction of the material within the extruder also provides a substantial amount of energy to the mixture and is required in the formation of a homogenous melt of the components. This result can be obtained conveniently in a twin screw compounder whose barrel sections can be heated and whose screws are made up from a series of conveying and kneading (or paddle) elements.

Spray-drying of a solution of the components also yields a solid dispersion of said components and may be a useful alternative to the melt-extrusion process, particularly in those cases where the water-soluble polymer or the lipid lowering agent would not be sufficiently stable to withstand the extrusion conditions and where residual solvent can be removed from the solid dispersion effectively. Yet another possible preparation consists of preparing a solution of the components, pouring said solution onto a large surface so as to form a thin film, and evaporating the solvent therefrom.

The solid dispersion product is milled or ground to particles having a particle size of less than 850 $\mu$m, preferably less than 500 $\mu$m and most preferably less than 125 $\mu$m. The particle size proves to be an important factor in the production of tablets having acceptable properties such as dissolution rate, hardness, friability and appearance. The particle size distribution is preferably such that more than 70% of the particles (measured by weight) have a diameter ranging from about 50 $\mu$m to about 500 $\mu$m, in particular from about 50 $\mu$m to about 200 $\mu$m and most in particular from about 50 $\mu$m to about 125 $\mu$m. Particles of the dimensions mentioned herein can be obtained by sieving them through nominal standard test sieves as described in the CRC Handbook, 64$^{th}$ ed., page F-114. Nominal standard sieves are characterized by the mesh/hole width ($\mu$m), DIN 4188 (mm), ASTM E 11-70 (No), Tyler® (mesh) or BS 410

(mesh) values. Throughout this description, and in the claims hereinafter, particle sizes are designated by reference to the mesh/hole width in mm and to the corresponding Sieve No. in the ASTM E11-70 standard.

Preferred are particles wherein the lipid lowering agent is in a non-crystalline phase as these have an intrinsically faster dissolution rate than those wherein part or all of the lipid lowering agent is in a microcrystalline or crystalline form.

Preferably, the solid dispersion is in the form of a solid solution comprising (a) and (b). Alternatively, it may be in the form of a dispersion wherein amorphous or microcrystalline (a) or amorphous or microcrystalline (b) is dispersed more or less evenly in a solid solution comprising (a) and (b).

The water-soluble polymer in the particles according to the present invention is a polymer that has an apparent viscosity of 1 to 100 mPa.s when dissolved in a 2% aqueous solution at 20° C. solution. For example, the water-soluble polymer can be selected from the group comprising alkylcelluloses such as methylcellulose, hydroxyalkylcelluloses such as hydroxymethylcellulose, hydroxyethylcellulose, hydroxypropylcellulose and hydroxybutylcellulose, hydroxyalkyl alkylcelluloses such as hydroxyethyl methylcellulose and hydroxypropyl methylcellulose, carboxyalkylcelluloses such as carboxymethylcellulose, alkali metal salts of carboxyalkylcelluloses such as sodium carboxymethylcellulose, carboxyalkylalkylcelluloses such as carboxymethylethylcellulose, carboxyalkylcellulose esters, starches, pectines such as sodium carboxymethylamylopectine, chitin derivates such as chitosan, polysaccharides such as alginic acid, alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol.

polyvinylpyrrolidone, copolymers of polyvinylpyrrolidone with vinyl acetate, polyalkylene oxides such as polyethylene oxide and polypropylene oxide and copolymers of ethylene oxide and propylene oxide.

Non-enumerated polymers which are pharmaceutically acceptable and have appropriate physico-chemical properties as defined hereinbefore are equally suited for preparing particles according to the present invention.

Preferred water-soluble polymers are hydroxypropyl methylcelluloses or HPMC, and copolymers of polyvinylpyrrolidone with vinyl acetate, in particular PVP-VA 64. Said HPMC contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule. Hydroxypropyl methylcellulose is the United States Adopted Name for hypromellose (see Martindale, The Extra Pharmacopoeia, 29th edition, page 1435). In the four digit number "2910", the first two digits represent the approximate percentage of methoxyl groups and the third and fourth digits the approximate percentage composition of hydroxypropoxyl groups; 5 mPa.s is a value indicative of the apparent viscosity of a 2% aqueous solution at 20° C.

The molecular weight of the HPMC normally affects both the release profile of the milled extrudate as well as its physical properties. A desired release profile can thus be designed by choosing an HPMC of an appropriate molecular weight; for immediate release of the active ingredient from the particles, a low molecular weight polymer is preferred. High molecular weight HPMC is more likely to yield a sustained release pharmaceutical dosage form. The molecular weight of a water-soluble cellulose ether is generally expressed in terms of the apparent viscosity at 20° C. of an aqueous solution containing two percent by weight of said polymer. Suitable HPMC include those having a viscosity from about 1 to about 100 mPa.s, in particular form about 3 to about 15 mPa.s, preferably about 5 mPa.s. The most preferred type of HPMC having a viscosity of 5 mPa.s., is the commercially available HPMC 2910 5 mPa.s, because this yields particles from which superior oral dosage forms of lipid lowering agent can be prepared as will be discussed hereunder and in the experimental part.

PVP-VA 64 is a vinylpyrrolidone—vinylacetate copolymer that is soluble in both water and alcohol, and is commercially available as Kollidon® VA 64 from BASF. The copolymer is derived from 1-vinyl-2-pyrrolidone and vinylacetate in a ratio of 6:4 by mass, and it is designated CAS nr 25086-89-9. The copolymer is particularly suited for use as a matrix material for rapid release formulations and can be melted and extruded readily with drugs having relatively poor bioavailability to form dispersions that dissolve rapidly.

The weight-by-weight ratio of (a):(b) is in the range of 1:1 to 1:35, preferably 1:1 to 1:5. In the case of (Compound A):(HPMC 2910 5 mPa.s), said ratio may range from about 1:1 to about 1:4, and optimally is about 1:3. The weight by weight ratio of lipid lowering agent to other water-soluble polymers may be determined by a person skilled in the art by straightforward experimentation. The lower limit is determined by practical considerations. Indeed, given the therapeutically effective amount of lipid lowering agent (from about 25 mg to about 200 mg, preferably about 150 mg per day), the lower limit of the ratio is determined by the maximum amount of mixture that can be processed into one dosage form of practical size. When the relative amount of water-soluble polymer is too high, the absolute amount of mixture needed to reach the therapeutic level will be too high to be processed into one capsule or tablet. Tablets, for example, have a maximum weight of about 1 g, and the extrudate can account for maximally about 90% (w/w) thereof. Consequently, the lower limit of the amount of lipid lowering agent over water-soluble polymer will be about 1:35 (25 mg lipid lowering agents +875 mg water-soluble polymer).

On the other hand, if the ratio is too high, this means the amount of lipid lowering agent is relatively high compared to the amount of water-soluble polymer, then there is the risk that the lipid lowering agent will not dissolve sufficiently in the water-soluble polymer, and thus the required bioavailability will not be obtained. The degree to which a compound has dissolved into a water-soluble polymer can often be checked visually: if the extrudate is clear then it is very likely that the compound will have dissolved completely in the water-soluble polymer. The 1:1 upper limit is determined by the fact that above said ratio it was observed that the extrudate resulting from extruding lipid lowering agent with HPMC 2910 5 mPa.s forms a solid solution, but appears to crystallize partially during milling. It will be appreciated that the upper limit of 1:1 may be underestimated for particular water-soluble polymers. Since this can be established easily but for the experimentation time involved, solid dispersions wherein the ratio (a):(b) is larger than 1:1 are also meant to be comprised within the scope of the present invention.

Preferred particles are those obtainable by melt-extrusion of the components and grinding, and optionally sieving. More in particular, the present invention concerns particles consisting of a solid solution comprising one part by weight of a lipid lowering agent, in particular Compound A, and from one to three parts by weight of hydroxy-propyl methylcellulose HPMC 2910 5 mPa.s, obtainable by blending said components, melt-extruding the blend at a temperature in the range of 120° C.–300° C., grinding the extrudate, and optionally sieving the thus obtained particles. The preparation is easy to perform and yields lipid lowering agent particles that are free of organic solvent.

The particle as described hereinabove may further comprise one or more pharmaceutically acceptable excipients such as, for example, disintegrants, plasticizers, flavors, colorants, preservatives and the like. Said excipients should not be heat-sensitive, in other words, they should not show any appreciable degradation or decomposition at the working temperature of the melt-extruder.

In the current lipid lowering agent: HPMC 2910 5 mPa.s formulations, the amount of plasticizer is preferably small, in the order of 0% to 15% (w/w), preferably less than 5% (w/w) and in particular 0% (w/w). With other water-soluble polymers though, plasticizers may be employed in much different, often higher amounts because plasticizers as mentioned hereinbelow lower the temperature at which a melt of (a), (b) and plasticizer is formed, and this lowering of the melting point is advantagous where the polymer has limited thermal stability. Suitable plasticizers are pharmaceutically acceptable and include low molecular weight polyalcohols such as ethylene glycol, propylene glycol, 1,2 butylene glycol, 2,3-butylene glycol, styrene glycol; polyethylene glycols such as diethylene glycol, triethylene glycol, tetraethylene glycol; other polyethylene glycols having a molecular weight lower than 1,000 g/mol; polypropylene glycols having a molecular weight lower than 200 g/mol; glycol ethers such as monopropylene glycol monoisopropyl ether; propylene glycol monoethyl ether; diethylene glycol monoethyl ether; ester type plasticizers such as sorbitol lactate, ethyl lactate, butyl lactate, ethyl glycolate, allyl glycollate; and amines such as monoethanolamine, diethanolamine, triethanolamine, monoisopropanolamine; triethylenetetramine, 2-amino-2-methyl- 1,3-propanediol and the like. Of these, the low molecular weight polyethylene glycols, ethylene glycol, low molecular weight polypropylene glycols and especially propylene glycol are preferred.

Once the extrudate is obtained, it is milled and sieved and used as a "normal" ingredient to make pharmaceutical dosage forms.

The particles of the present invention can be formulated into pharmaceutical dosage forms comprising a therapeutically effective amount of particles. Although, at first instance, pharmaceutical dosage forms for oral administration such as tablets and capsules are envisaged, the particles of the present invention can also be used to prepare pharmaceutical dosage forms e.g. for rectal administration. Preferred dosage forms are those adapted for oral administration shaped as a tablet or a capsule.

Tablets can be produced by conventional tabletting techniques with conventional ingredients or excipients and with conventional tabletting machines. In addition, they can be produced at low cost. As mentioned above, an effective daily dose of lipid lowering agent such as Compound A ranges from about 25 mg to about 200 mg o.d., and preferably is about 100 to about 150 mg o.d. When one considers that the weight-by-weight ratio of (a):(b) is maxim ally about 1:1, then it follows that one dosage form will weigh at least 90 mg. The shape of the tablets may be round, oval or oblong. In order to facilitate the swallowing of large dosage forms by a patient, it is advantageous to give the tablets an appropriate shape. Tablets that can be swallowed comfortably are therefore preferably elongated rather than round in shape. Especially preferred are biconvex oblate tablets. As discussed hereunder in more detail, a film coat on the tablet further contributes to the ease with which it can be swallowed.

Tablets that give an immediate release of lipid lowering agent upon oral ingestion and that have good bioavailability are designed in such a manner that the tablets disintegrate rapidly in the stomach (immediate release) and that the particles which are liberated thereby are kept away from one another so that they do not coalesce, give local high concentrations of lipid lowering agent and the chance that the drug precipitates (bioavail-ability). The desired effect can be obtained by distributing said particles homogeneously throughout a mixture of a disintegrant and a diluent. Alternatively, part of the disintegrant and diluent may be admixed with the physical mixture of the lipid lowering agent of formula (I) and the water-soluble polymer, and processed such that the particles obtained thereby consist of a solid solution comprising an internal disintegrant and diluent.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose (crosslinked sodium carboxymethylcellulose). The amount of disintegrant in immediate release tablets according to the present invention may conveniently range from about 3 to about 15% (w/w) and preferably is about 7 to 9%, in particular about 8.5% (w/w). This amount tends to be larger than usual in tablets in order to ensure that the particles are spread over a large volume of the stomach contents upon ingestion. Because disintegrants by their nature yield sustained release formulations when employed in bulk, it is advantageous to dilute them with an inert substance called a diluent or filler.

A variety of materials may be used as diluents or fillers. Examples are spray-dried or anhydrous lactose, sucrose, dextrose, mannitol, sorbitol, starch, cellulose (e.g. microcrystalline cellulose Avicel™), dihydrated or anhydrous dibasic calcium phosphate, and others known in the art, and mixtures thereof. Preferred is a commercial spray-dried mixture of lactose monohydrate (75%) with microcrystalline cellulose (25%) which is commercially available as Microcelac™. The amount of diluent or filler in the tablets may conveniently range from about 20% to about 40% (w/w) and preferably ranges from about 25% to about 32% (w/w).

The tablet may include a variety of one or more other conventional excipients such as binders, buffering agents, lubricants, glidants, thickening agents, sweetening agents, flavors, and colors. Some excipients can serve multiple purposes.

Lubricants and glidants can be employed in the manufacture of certain dosage forms, and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, talc, mixtures thereof, and others known in the art. Interesting lubricants and glidants are magnesium stearate, and mixtures of magnesium stearate with colloidal silica. A preferred lubricant is hydrogenated vegetable oil type I (micronized), most preferably hydrogenated, deodorized Cottonseed oil (commercially available from Karlshamns as Akofine NF™ (formerly called Sterotex™)). Lubricants and glidants generally comprise 0.2 to 7.0% of the total tablet weight.

Other excipients such as coloring agents and pigments may also be added to the tablets of the present invention. Coloring agents and pigments include titanium dioxide and dyes suitable for food. A coloring agent is an optional ingredient in the tablet of the present invention, but when used the coloring agent can be present in an amount up to 3.5% based on the total tablet weight.

Flavors are optional in the composition and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, eucalyptus, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth. The amount of flavor may depend on a number of factors including the organoleptic effect desired. Generally the flavor will be present in an amount from about 0% to about 3% (w/w).

As known in the art, tablet blends may be dry-granulated or wet-granulated before tabletting. The tabletting process itself is otherwise standard and readily practised by forming a tablet from desired blend or mixture of ingredients into the appropriate shape using a conventional tablet press.

Tablets of the present invention may further be film-coated to improve taste, to provide ease of swallowing and an elegant appearance. Many suitable polymeric film-coating materials are known in the art. A preferred film-coating material is hydroxypropyl methylcellulose HPMC, especially HPMC 2910 5 mpa.s. Other suitable film-forming polymers also may be used herein, including, hydroxypropylcellulose, and acrylatemethacrylate copolymers. Besides a film-forming polymer, the film coat may further comprise a plasticizer (e.g. propylene glycol) and optionally a pigment (e.g. titanium dioxide). The film-coating suspension also may contain talc as an anti-adhesive. In immediate release tablets according to the invention, the film coat is small and in terms of weight accounts for less than about 3.5% (w/w) of the total tablet weight.

Preferred dosage forms are those wherein the weight of the particles ranges from 40% to 60% of the total weight of the total dosage form, that of the diluent ranges from 20% to 40%, and that of the disintegrant ranges from 3 to 10%, the remainder being accounted for by one or more of the excipients described hereinabove.

As an example of a preferred oral dosage form comprising 100 mg of Compound A, the following formula may be given:

```
13.44%  Compound A (100 mg)
40.32%  HPMC 2910 5 mPa.s (300 mg)
30.38%  spray-dried lactose monohydrate:microcrystalline cellulose
        (75:25) mixture (226 mg)
 8.44%  crospolyvidone (62.8 mg)
 2.77%  talc (20.6 mg)
 0.91%  hydrogenated vegetable oil Type I (6.8 mg)
 0.27%  colloidal anhydrous silica (2 mg)
 0.23%  magnesium stearate (1.8 mg), yielding
96.77%  tablet core (720 mg), and
 1.84%  HPMC 2910 5 mPa.s (13.7 mg)
 0.46%  propylene glycol (3.282 μl) (3.4 mg)
 0.37%  talc (2.76 mg)
 0.56%  titanium dioxide (4.14 mg), yielding
 3.23%  film-coat (24 mg), together forming
  100%  film-coated tablet (744 mg).
```

As an example of a further preferred oral dosage form comprising 25 mg of Compound A, the following formula may be given:

```
27.8%   Compound A (25 mg)
27.8%   HPMC 2910 5 mPa.s (25 mg)
30.38%  spray-dried lactose monohydrate:microcrystalline cellulose
        (75:25) mixture (28.25 mg)
 8.44%  crospolyvidone (7.85 mg)
 2.77%  talc (2.575 mg)
 0.91%  hydrogenated vegetable oil Type I (0.85 mg)
 0.27%  colloidal anhydrous silica (0.25 mg)
 0.23%  magnesium stearate (0.225 mg), yielding
96.77%  tablet core (90 mg), and
 1.84%  HPMC 2910 5 mPa.s (1.7125 mg)
 0.46%  propylene glycol (0.41025 μl) (0.425 mg)
 0.37%  talc (0.345 mg)
 0.56%  titanium dioxide (0.5175 mg), yielding
 3.23%  film-coat (3 mg), together forming
  100%  film-coated tablet (93 mg).
```

Capsules can be produced by filling an appropriate amount of the melt extrudate particles into a capsule of suitable size using a standard automatic capsule filling machine. In order to prevent the particles from adhering to one another, they are advantageously coated with a seal coating polymer layer. Particles having a particle size of less than 1,000 μm, particularly less than 850 μm, and more than 500 μm, particularly more than 600 μm are preferred because they are easy to sela coat and fill into capsules. Particles of the dimensions mentioned herein can be obtained by sieving them through nominal standard test sieves as described in the CRC Handbook, 64$^{th}$ ed., page F-114. Nominal standard sieves are characterized by the mesh/hole width (μm), DIN 4188 (mm), ASTM E 11-70 (No), Tyler® (mesh) or BS 410 (mesh) values. Throughout this description, and in the claims hereinafter, particle sizes are designated by reference to the mesh/hole width in mm and to the corresponding Sieve No. in the ASTM E11-70 standard.

The seal coating polymer layer is applied to the particles in a fluidized bed granulator with Wurster bottom spray insert. The seal coating solution can be prepared by dissolving an appropriate amount of a seal coating polymer into a suitable solvent system. Such a system is, for example, methylene chloride optionally admixed with an alcohol, e.g. ethanol which may be denatured with, for example, butanone. The amount of seal coating polymer in the seal coating spraying solution may range from 7 to 12% (w/w) and preferably is about 10%. The seal coating spraying solution is advantageously stirred during the seal coating process. Appropriate conditions are described in more detail in the example hereinafter.

The seal coating process are preferably conducted under an inert atmosphere of e.g. nitrogen. The coating equipment should preferably be grounded and provided with an appropriate solvent recovery system containing an efficient condensing system.

Capsule filling speed may influence weight distribution and should be monitored. Good results are obtained when operating the equipment at about 75% to 85% of the maximum speed and in many cases when operating at full speed.

Preferred dosage forms according to the present invention are those from which at least 40% of the available lipid lowering agent dissolves within 60 minutes when a dosage form equivalent to 100 μg lipid lowering agent is tested as set forth in USP test <711> in a USP-2 dissolution apparatus under conditions at least as stringent as the following: 900 ml 0.1 N HCl, 37° C. with paddles turning at 75 rpm. Tablets complying with the preceding definition can be said to have Q>40% (60'). Preferably, tablets according to the present invention will dissolve faster and have Q>75% (60'), more preferably Q>75% (45').

The present invention further concerns a process of preparing particles as described hereinbefore, characterized by blending the components, extruding said blend at a temperature in the range of 120° C.–300° C., preferably in the range of 170° C.–230° C, in particular in the range of 180° C.–220° C., grinding the extrudate, and optionally sieving the particles.

The invention also concerns solid dispersions obtainable by melt-extrusion of
  (a) a lipid lowering agent of formula (I), a stereoisomer or a mixture of two or more stereoisomers, and
  (b) one or more pharmaceutically acceptable water-soluble polymers.

It is another object of the invention to provide a process of preparing a pharmaceutical dosage form as described hereinbefore, characterized by blending a therapeutically effective amount of particles as described hereinbefore, with pharmaceutically acceptable excipients and compressing said blend into tablets.

Further, this invention concerns particles as described hereinbefore, for use in preparing a pharmaceutical dosage form for oral administration to a mammal suffering from hyperlipidemia, obesitas or atherosclerosis, wherein a single such dosage form can be administered once daily to said mammal.

The invention also relates to particles as described hereinbefore, for use in preparing a pharmaceutical dosage form for oral administration to a mammal suffering from hyperlipidemia, obesitas or atherosclerosis, wherein said dosage form can be administered at any time of the day independently of the food taken in by said mammal.

The present invention also concerns the use of particles according to as described hereinbefore, for the preparation of a pharmaceutical dosage form for oral administration to a mammal suffering from hyperlipidemia, obesitas or atherosclerosis, wherein a single such dosage form can be administered once daily to said mammal.

The present invention also concerns the use of particles as described hereinbefore, for the preparation of a pharmaceutical dosage form for oral administration to a mammal suffering from hyperlipidemia, obesitas or atherosclerosis, wherein said dosage form can be administered at any time of the day independently of the food taken in by said mammal.

The invention also relates to a method of treating hyperlipidemia, obesitas or atherosclerosis in a mammal which comprises administering to said mammal an effective amount of lipid lowering agent in a single oral dosage form which can be administered once daily.

The invention also relates to a method of treating hyperlipidemia, obesitas or atherosclerosis in a mammal which comprises administering to said mammal an effective amount of lipid lowering agent in a single oral dosage form which can be administered at any time of the day independently of the food taken in by said mammal.

The invention also relates to a pharmaceutical package suitable for commercial sale comprising a container, an oral dosage form of lipid lowering agent as described hereinbefore, and associated with said package written matter non-limited as to whether the dosage form can be taken with or without food.

Experimental Part

The following tables show the formulas of the compounds of formula (I), their physical data, and references to the examples in WO-96/13499 according to which the compounds in question may be prepared. In the pharmacological example, the lipid lowering effect of the compounds of formula (I) is illustrated. Then follow examples demonstrating how Compound A (compound 40) can be converted into a solid solution and formulated into a solid dosage form having good bioavailability.

TABLE 1

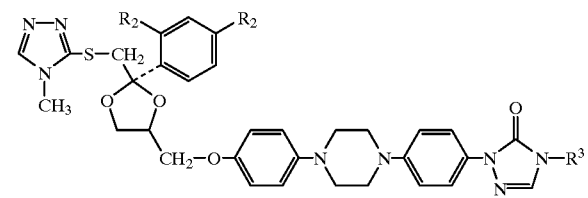

| Co. No | Ex. No. | R¹ | R² | R³ | physical data |
|---|---|---|---|---|---|
| 1 | 3 | Cl | H | CH(CH₃)₂ | mp. 194.8° C./cis |
| 2 | 3 | Cl | H | CH(CH₃)CH₂CH₃ | mp. 147.8° C./cis |
| 3 | 3 | Cl | H | CH₂—CH(CH₃)₂ | mp. 182.5° C./cis |
| 4 | 4 | F | H | CH(CH₃)₂ | mp. 181.1° C./cis |
| 5 | 4 | F | H | CH₂—CH(CH₃)₂ | mp. 166.4° C./cis |
| 6 | 3 | Cl | H | cyclo(C₅H₉) | mp. 198.8° C./cis |
| 7 | 3 | Cl | H | CH(CH₂CH₃)₂ | mp. 139.6° C./cis |
| 8 | 3 | Cl | H | (CH₂)₂CH₃ | mp. 184.6° C./cis |
| 9 | 4 | F | H | CH(CH₃)CH₂CH₃ | mp. 180.0° C./cis |
| 10 | 4 | F | F | CH(CH₃)CH₂CH₃ | mp. 180.7° C./cis |
| 11 | 4 | F | H | cyclo(C₅H₉) | mp. 194.2° C./cis |
| 12 | 4 | F | H | CH(CH₂CH₃)₂ | mp. 144.3° C./cis |
| 13 | 4 | F | F | cyclo(C₅H₉) | mp. 202.4° C./cis |
| 14 | 4 | F | F | CH(CH₂CH₃)₂ | mp. 166.7° C./cis |
| 15 | 3 | Cl | H | (CH₂)₃CH₃ | mp. 194.6° C./cis |
| 16 | 3 | Cl | H | CH₂—CH₃ | mp. 218.3° C./cis |
| 17 | 3 | Cl | H | CH₂—CH(OH)—C(CH₃)₃ | mp. 205.9° C./cis |
| 18 | 3 | Cl | H | (CH₂)₄CH₃ | mp. 173.8° C./cis |
| 19 | 4 | Cl | H | CH(CH₃)CH₂CH₃ | mp. 140.9° C./trans |
| 20 | 4 | Cl | H | CH₃ | mp. 208.6° C./cis |
| 21 | 4 | Cl | H | CH(CH₃)CH(OH)(CH₃) | mp. 202.4° C./cis |
| 133 | 3 | CH₃ | H | (CH₂)₄CH₃ | mp. 147.4° C./cis |
| 134 | 3 | Br | H | (CH₂)₄CH₃ | mp. 152.5° C./cis |
| 136 | 3 | Cl | H | cyclo(C₅H₉) | 2S-cis |
| 137 | 3 | Cl | H | (CH₂)₄CH₃ | 2S-cis |

TABLE 2
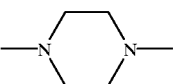
| Co. No | Ex. No. | R¹ | R² | R³ | —X— | physical data |
|---|---|---|---|---|---|---|
| 22 | 3 | Cl | H | CH(CH$_3$)CH$_2$CH$_3$ | 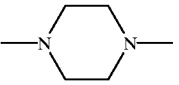 | mp. 176.9° C./cis |
| 23 | 3 | Cl | H | CH$_2$CH(CH$_3$)$_2$ |  | mp. 192.9° C./cis |
| 24 | 3 | Cl | H | cyclo(C$_5$H$_9$) |  | mp. 210.2° C./cis |
| 25 | 4 | F | H | CH$_2$CH(CH$_3$)$_2$ |  | mp. 180.6° C./cis |
| 26 | 3 | Cl | H | (CH$_2$)$_3$CH$_3$ |  | mp. 194.1° C./cis |
| 27 | 3 | Cl | H | (CH$_2$)$_2$CH$_3$ |  | mp. 187.3° C./cis |
| 28 | 4 | F | H | CH(CH$_3$)CH$_2$CH$_3$ |  | mp. 157.5° C./cis |
| 29 | 4 | F | F | CH(CH$_3$)CH$_2$CH$_3$ |  | mp. 146.4° C./cis |
| 30 | 3 | Cl | H | CH$_2$—CH$_3$ |  | mp. 195.5° C./cis |
| 31 | 3 | Cl | H | CH$_3$ |  | mp. 161.2° C./cis |
| 32 | 4 | Cl | H | (CH$_2$)$_4$CH$_3$ |  | mp. 191.7° C./cis |

TABLE 2-continued

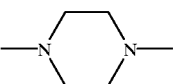

| Co. No | Ex. No. | R¹ | R² | R³ | —X— | physical data |
|---|---|---|---|---|---|---|
| 33 | 4 | Cl | H | CH(CH₃)₂ | piperazine | mp. 157.2° C./cis |
| 34 | 4 | Cl | H | CH₂—CH(OH)—C(CH₃)₃ | piperazine | mp. 189.9° C./cis |
| 35 | 4 | F | H | cyclo(C₅H₉) | piperazine | mp. 198.2° C./cis |
| 36 | 4 | Cl | H | CH(CH₃)CH₂CH₃ | piperazine | mp. 180.7° C./trans |
| 37 | 4 | F | F | cyclo(C₅H₉) | piperazine | mp. 185.2° C./cis |
| 38 | 3 | Cl | H | CH(CH₃)CH₂CH₃ | piperazine | mp. 187.0° C./ [α]$_D^{20}$ = −24.5° (c = 0.5% in DMF) (−)-[2S-[2α,4α(R*)]] |
| 39 | 3 | Cl | H | CH(CH₃)CH₂CH₃ | piperazine | mp. 155.1° C./ [α]$_D^{20}$ = +34.64° (c = 0.5% in DMF) (+)-[2R-[2α,4α(S*)]] |
| 40A | 3 | Cl | H | CH(CH₃)CH₂CH₃ | piperazine | mp. 156.4° C./ [α]$_D^{20}$ = −33.1° (c = 0.5% in DMF) (−)-[2S-[2α,4α(S*)]] |
| 41 | 3 | Cl | H | CH(CH₃)CH₂CH₃ | piperazine | mp. 187.7° C./ [α]$_D^{20}$ = +24.65° (c = 0.5% in DMF) (+)-[2R-[2α,4α(R*)]] |
| 42 | 3 | F | H | (CH₂)₂CH(CH₃)₂ | piperazine | mp. 176.4° C./cis |
| 43 | 3 | F | H | CH(CH₂CH₃)₂ | piperazine | mp. 145.6° C./cis |

TABLE 2-continued

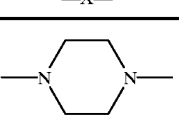

| Co. No | Ex. No. | R¹ | R² | R³ | —X— | physical data |
|---|---|---|---|---|---|---|
| 44 | 4 | Cl | H | CH(CH₂CH₃)₂ | piperazine | mp. 156.7° C./cis |
| 45 | 4 | F | F | (CH₂)₂CH(CH₃)₂ | piperazine | mp. 176.8° C./cis |
| 46 | 3 | F | F | CH(CH₂CH₃)₂ | piperazine | mp. 118.6° C./cis |
| 47 | 4 | Cl | H | CH(CH₃)COCH₃ | piperazine | mp. 157.6° C./cis |
| 48 | 6 | Cl | H | CH(CH₃)CH(OH)CH₃ | piperazine | mp. 153.4° C./cis |
| 135 | 3 | Cl | H | CH(CH₃)CH₂CH₃ | piperazine N-oxide | cis |

TABLE 3

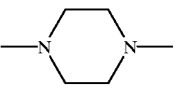

cis

| Co. No. | Ex. No. | R⁹ | R⁸ | physical data |
|---|---|---|---|---|
| 49 | 3 | CF₃ | H | mp. 133.3° C. |
| 50 | 3 | CF₃ | CH₃ | mp. 159.6° C. |
| 51 | 3 | H | (CH₂)₃CH₃ | mp. 173.5° C. |
| 52 | 3 | H | CH(CH₃)₂ | mp. 159.1° C. |
| 53 | 3 | H | CH₂CH₃ | mp. 175.6° C. |
| 54 | 3 | H | CH₂CH(CH₃)₂ | mp. 186.4° C. |
| 55 | 3 | H | (CH₂)₂CH₃ | mp. 168.5° C. |
| 56 | 3 | CH₃ | CH₃ | mp. 170.0° C. |
| 57 | 3 | NH₂ | H | — |

TABLE 3-continued

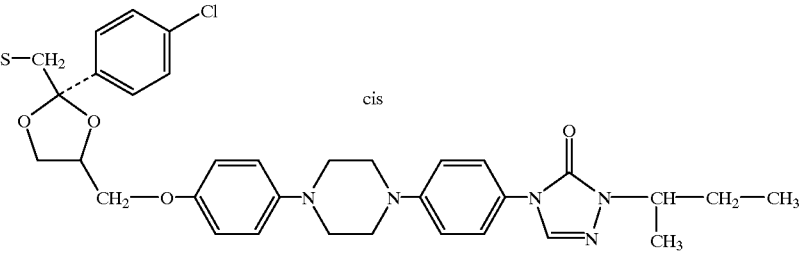

| Co. No. | Ex. No. | $R^9$ | $R^8$ | physical data |
|---|---|---|---|---|
| 58 | 3 | OH | $CH_3$ | — |
| 59 | 3 | OH | $CH(CH_3)_2$ | — |

TABLE 4

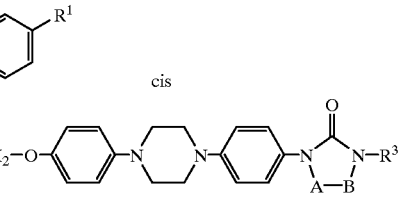

| Co. No. | Ex. No. | $R^1$ | $R^2$ | $R^3$ | A—B | physical data |
|---|---|---|---|---|---|---|
| 60 | 3 | Cl | H | $CH(CH_3)CH_2CH_3$ | CH=N | mp. 147.7° C. |
| 61 | 3 | Cl | H | $CH_2CH(CH_3)_2$ | CH=N | mp. 159.4° C. |
| 62 | 4 | F | F | $CH(CH_3)CH_2CH_3$ | CH=N | mp. 100.6° C. |
| 63 | 4 | F | H | $CH(CH_3)CH_2CH_3$ | CH=N | mp. 138.8° C. |
| 64 | 3 | F | H | $CH(CH_2CH_3)_2$ | CH=N | mp. 132.3° C. |
| 65 | 3 | F | F | $CH(CH_2CH_3)_2$ | CH=N | mp. 120.4° C. |
| 66 | 3 | F | H | $cyclo(C_5H_9)$ | CH=N | mp. 163.0° C. |
| 67 | 3 | F | F | $cyclo(C_5H_9)$ | CH=N | mp. 150.7° C. |
| 68 | 3 | Cl | H | $CH(CH_3)_2$ | N=CH | mp. 170.1° C. |

TABLE 4-continued

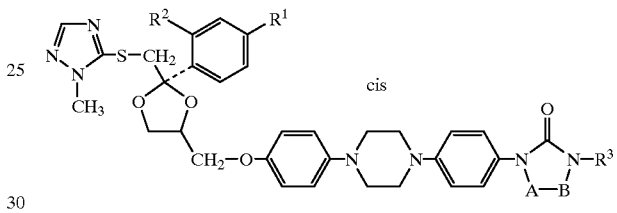

| Co. No. | Ex. No. | $R^1$ | $R^2$ | $R^3$ | A—B | physical data |
|---|---|---|---|---|---|---|
| 69 | 3 | Cl | H | $CH(CH_3)CH_2CH_3$ | N=CH | mp. 176.2° C. |
| 70 | 4 | F | H | $CH(CH_3)CH_2CH_3$ | N=CH | mp. 157.3° C. |
| 71 | 4 | F | F | $CH(CH_3)CH_2CH_3$ | N=CH | mp. 162.4° C. |
| 72 | 4 | F | F | $cyclo(C_5H_9)$ | N=CH | mp. 183.3° C. |
| 73 | 4 | F | F | $CH(CH_2CH_3)_2$ | N=CH | mp. 158.9° C. |
| 74 | 3 | F | H | $cyclo(C_5H_9)$ | N=CH | mp. 201.2° C. |
| 75 | 3 | F | H | $CH(CH_2CH_3)_2$ | N=CH | mp. 117.4° C. |

TABLE 5

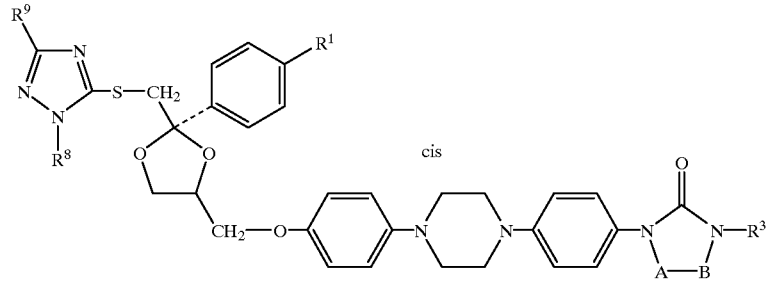

| Co. No. | Ex. No. | $R^9$ | $R^8$ | $R^1$ | A—B | $R^3$ | physical data |
|---|---|---|---|---|---|---|---|
| 76 | 3 | H | H | Cl | CH=N | $CH(CH_3)CH_2CH_3$ | mp. 179.6° C. |
| 77 | 3 | H | $CH_2CH_3$ | Cl | CH=N | $CH(CH_3)CH_2CH_3$ | mp. 119.3° C. |
| 78 | 3 | $CH_2CH_3$ | $(CH_2)_2CH_3$ | Cl | CH=N | $CH(CH_3)CH_2CH_3$ | mp. 97.8° C. |
| 79 | 3 | H | $(CH_2)_3CH_3$ | Cl | CH=N | $CH(CH_3)CH_2CH_3$ | mp. 108.6° C. |
| 80 | 3 | H | $(CH_2)_2CH_3$ | Cl | CH=N | $CH(CH_3)CH_2CH_3$ | mp. 87.3° C. |
| 81 | 3 | $CH_3$ | $CH_3$ | Cl | CH=N | $CH(CH_3)CH_2CH_3$ | mp. 85.6° C. |
| 82 | 5 | H | $CH(CH_3)_2$ | Cl | CH=N | $CH(CH_3)CH_2CH_3$ | mp. 141.2° C. |
| 83 | 3 | H | H | Cl | N=CH | $CH(CH_3)CH_2CH_3$ | mp. 160.1° C. |
| 84 | 3 | H | H | Cl | N=CH | $CH_2CH(CH_3)_2$ | mp. 160.6° C. |
| 85 | 5 | H | $CH(CH_3)_2$ | Cl | N=CH | $CH(CH_3)CH_2CH_3$ | mp. 134.9° C. |
| 86 | 3 | H | H | F | CH=N | $CH(CH_3)CH_2CH_3$ | mp. 101.3° C. |

TABLE 5-continued

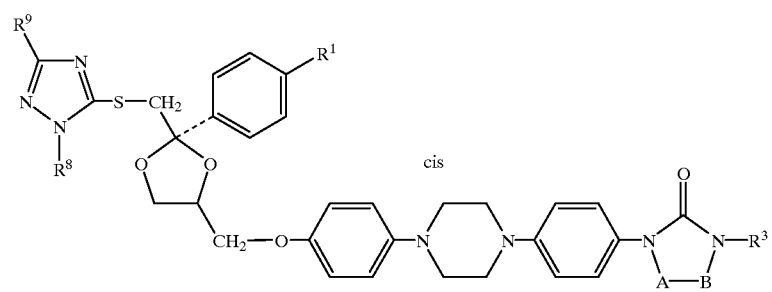

| Co. No. | Ex. No. | R⁹ | R⁸ | R¹ | A—B | R³ | physical data |
|---|---|---|---|---|---|---|---|
| 87 | 3 | H | CH₃ | Cl | N=CH | CH₂CH(CH₃)₂ | mp. 154.3° C. |
| 114 | 3 | H | CH₃ | Cl | CH=CH | CH(CH₃)CH₂CH₃ | mp. 125.2° C. |
| 115 | 3 | H | CH₃ | Cl | CH=CH | CH(C₂H₅)CH₂CH₃ | mp. 147.7° C. |
| 116 | 3 | H | CH₃ | Cl | CH=CH | cyclo(C₅H₉) | mp. 154.2° C. |
| 117 | 3 | H | H | Cl | CH=CH | CH(CH₃)CH₂CH₃ | mp. 186.8° C. |
| 118 | 3 | H | CH₃ | F | CH=CH | CH(C₂H₅)CH₂CH₃ | mp. 134.1° C. |
| 119 | 3 | H | CH₃ | Cl | CH=N | cyclo(C₅H₉) | mp. 161.1° C. |
| 120 | 5 | H | CH(CH₃)₂ | Cl | CH=CH | CH(CH₃)CH₂CH₃ | mp. 137.5° C. |
| 121 | 3 | H | CH₃ | F | CH=CH | cyclo(C₅H₉) | mp. 166.2° C. |

TABLE 6

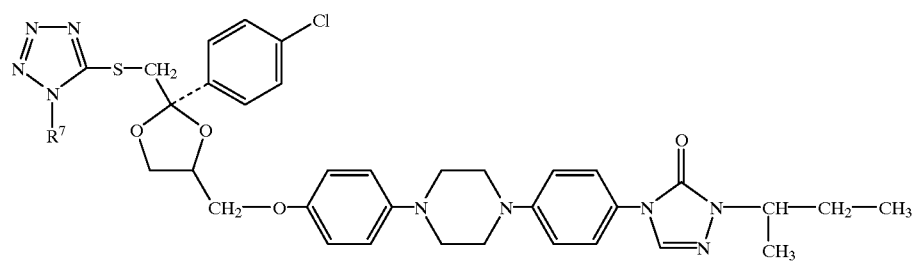

| Co. No. | Ex. No. | R⁷ | physical data |
|---|---|---|---|
| 88 | 3 | CH₃ | — |
| 89 | 3 | phenyl | — |

TABLE 7

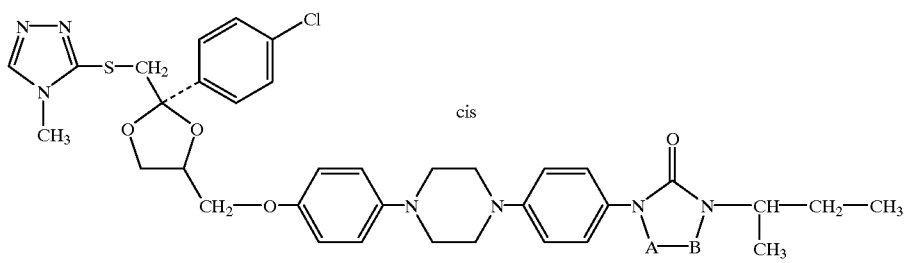

| Co. No. | Ex. No. | A—B | physical data |
|---|---|---|---|
| 90 | 3 | C(CH₃)=N | mp. 98.3° C./1/2 H₂O |
| 91 | 3 | C(CH₃)₂CO | mp. 96.0° C. |
| 92 | 3 | CO—C(CH₃)₂ | mp. 127.1° C. |
| 93 | 4 | CH=CH | mp. 171.8° C. |
| 94 | 4 | CH₂—CH₂ | mp. 147.3° C. |

TABLE 8

| Co. No. | Ex. No. | R¹² | A—B | R² | physical data |
|---|---|---|---|---|---|
| 95 | 3 | $CH_3$ | CH=N | $CH(CH_3)CH_2CH_3$ | mp. 134.2° C. |
| 96 | 3 | $CH_3$ | CH=N | $CH_2CH(CH_3)_2$ | mp. 164.9° C. |
| 97 | 3 | H | CH=N | $CH(CH_3)CH_2CH_3$ | — |
| 98 | 3 | $CH_3$ | N=CH | $CH(CH_3)_2$ | mp. 187.7° C. |

TABLE 8-continued

| Co. No. | Ex. No. | R¹² | A—B | R² | physical data |
|---|---|---|---|---|---|
| 99 | 3 | $CH_3$ | N=CH | $CH(CH_3)CH_2CH_3$ | mp. 150.4° C. |
| 100 | 3 | $CH_3$ | N=CH | $CH_2CH(CH_3)_2$ | mp. 146.8° C. |

TABLE 9

| Co. No. | Ex. No. | R⁵ | R⁶ | physical data |
|---|---|---|---|---|
| 101 | 3 | H | H | mp. 159.6° C. |
| 102 | 3 | $CH_3$ | $CH_3$ | mp. 157.4° C. |
| 103 | 3 | $NH_2$ | $NH_2$ | mp. 248.5° C. |

TABLE 10

| Co. No. | Ex. No. | Het | A—B | R³ | physical data |
|---|---|---|---|---|---|
| 104 | 3 | 5-methyl-1,3,4-thiadiazol-2-yl | CH=N | $CH(CH_3)CH_2CH_3$ | — |
| 105 | 3 | 2-pyridinyl | CH=N | $CH(CH_3)CH_2CH_3$ | mp. 154.1° C. |
| 106 | 3 | 4-pyridinyl | CH=N | $CH(CH_3)CH_2CH_3$ | mp. 174.9° C. |
| 107 | 3 | 4-methyl-2-oxazolyl | CH=N | $CH(CH_3)CH_2CH_3$ | mp. 115.3° C. |
| 108 | 3 | 2-thiazolyl | CH=N | $CH(CH_3)CH_2CH_3$ | mp. 158.6° C. |
| 109 | 3 | 4-oxo-2-thiazolyl | CH=N | $CH(CH_3)CH_2CH_3$ | — |
| 110 | 3 | 2-thiazolyl | N=CH | $CH(CH_3)CH_2CH_3$ | mp. 157.8° C. |
| 111 | 3 | 2-thiazolyl | N=CH | $CH_2CH(CH_3)_2$ | mp. 167.9° C. |
| 112 | 5 | (1-methylethyl)-2H-1,2,4-triazol-3-yl | CH=N | $CH(CH_3)CH_2CH_3$ | mp. 128.8° C. |
| 113 | 5 | (1-methylethyl)-1H-1,2,4-triazol-3-yl | N=CH | $CH(CH_3)CH_2CH_3$ | mp. 150.0° C. |
| 122 | 3 | 4-methyl-4H-1,2,4-triazol-3-yl | CH=CH | $CH(C_2H_5)CH_2CH_3$ | mp. 134.4° C. |
| 123 | 3 | 4-methyl-4H-1,2,4-triazol-3-yl | CH=CH | cyclo($C_5H_9$) | mp. 202.8° C. |
| 124 | 5 | (1-methylethyl)-1H- | CH=CH | $CH(CH_3)CH_2CH_3$ | mp. 155.7° C. |

TABLE 10-continued

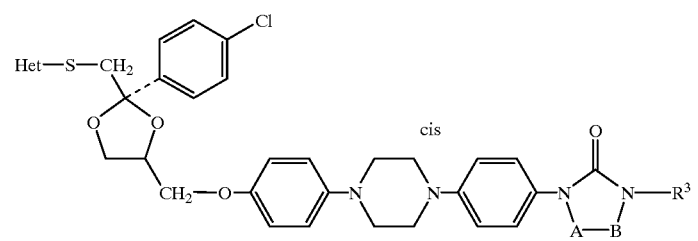

| Co. No. | Ex. No. | Het | A—B | R³ | physical data |
|---|---|---|---|---|---|
| 125 | 3 | 1,2,4-triazol-3-yl 4-methyl-4H-1,2,4-triazol-3-yl | CH=N | CH(C₂H₅)CH₂CH₃ | mp. 123.2° C. |

TABLE 11

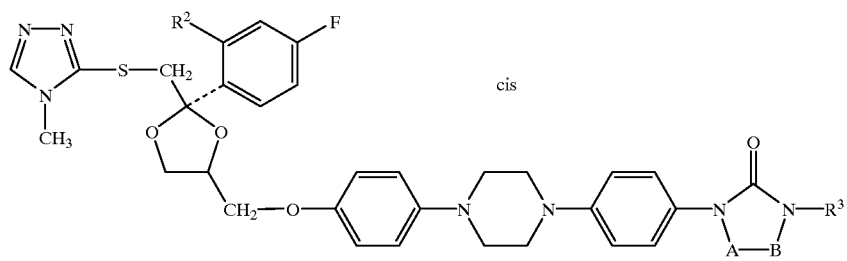

| Co. No. | Ex. No. | R₂ | R₃ | A-B | physical data |
|---|---|---|---|---|---|
| 126 | 3 | H | CH(CH₃)CH₂CH₃ | CH=CH | mp. 175.4° C. |
| 127 | 3 | F | CH(CH₃)CH₂CH₃ | CH=CH | mp. 155.5° C. |
| 128 | 3 | H | cyclo(C₅H₉) | CH=CH | mp. 192.0° C. |
| 129 | 3 | F | cyclo(C₅H₉) | CH=CH | mp. 181.8.C |
| 130 | 3 | H | CH(C₂H₅)CH₂CH₃ | CH=CH | mp. 145.5° C. |
| 131 | 3 | F | CH(C₂H₅)CH₂CH₃ | CH=CH | mp. 139.1° C. |
| 132 | 3 | H | (CH₂)₄CH₃ | N=CH | mp. 153.1° C. |

Pharmacology

EXAMPLE 1

Apolipoprotein B (apo B) Inhibition Test

Cultured human liver cells (Hep G2-cells) which synthesize and secrete low-density lipoproteins, were incubated overnight at 37° C. in a liquid medium containing radioactively labelled leucine. Thus radioactively labelled leucine was incorporated into the apolipoprotein B. The liquid medium was decanted and the apolipoprotein B was isolated by means of a double immunoprecipitation, i.e. first an apolipoprotein B-specific antibody (antibody₁) was added to the liquid medium and subsequently a second antibody (antibody₂) was added which binds specifically to the apoB-antibody₁-complex. The thus formed apoB-antibody₁-antibody₂ complex precipitated and was isolated by centrifuge. Quantification of the amount of apolipoprotein B synthesized during the night resulted from measuring the radioactivity of the isolated complex. To measure the inhibiting activity of the test compound, that test compound was added to the liquid medium at different concentrations and the concentration of apolipoprotein B synthesized in the presence of a test compound (concentration apoB(after)) was compared to the concentration of apolipoprotein B which was synthesized in the absence of the test compound (concentration apoB(control)). For each experiment the inhibition of apolipoprotein-B formation was expressed as $$\% \text{ inhibition} = 100 \times \frac{1 - \text{concentration of } apoB \text{ (after)}}{\text{concentration } apoB \text{ (control)}}$$

When more experiments were carried out for the same concentration, the median value of the inhibition calculated for these experiments was calculated. IC₅₀-values (concentration of the drug needed to reduce apoB secretion to 50% of the control) were also computed.

Table 12 lists the IC₅₀-values for some of the exemplified compounds of formula (I). Exemplified compounds of formula (I) that are not listed in Table 12, and for which data is available, have an IC₅₀-value of 1×10⁻⁶ M or more.

TABLE 12

| Comp. No. | IC₅₀ (× 10⁻⁸ M) |
|---|---|
| 1 | 9.2 |

TABLE 12-continued

| Comp. No. | IC$_{50}$ (× 10$^{-8}$ M) |
|---|---|
| 2 | 4.7 |
| 3 | 9.1 |
| 4 | 26 |
| 5 | 20 |
| 6 | 12 |
| 7 | 7.9 |
| 8 | 13 |
| 9 | 11 |
| 12 | 19 |
| 13 | 51 |
| 15 | 4.8 |
| 18 | 4.1 |
| 22 | 7.1 |
| 23 | 14 |
| 24 | 5.8 |
| 28 | 9.7 |
| 32 | 18 |
| 33 | 9.1 |
| 35 | 7.7 |
| 37 | 23 |
| 38 | 6.5 |
| 40 | 2.3 |
| 43 | 11 |
| 44 | 5.1 |
| 49 | 85 |
| 50 | 26 |
| 51 | 4.7 |
| 52 | 25 |
| 53 | 8.4 |
| 54 | 7.9 |
| 55 | 7.8 |
| 56 | 23 |
| 58 | 31 |
| 60 | 4.6 |
| 61 | 8.1 |
| 62 | 19 |
| 63 | 4.6 |
| 64 | 16 |
| 65 | 29 |
| 66 | 13 |
| 67 | 18 |
| 68 | 8.1 |
| 69 | 2.6 |
| 71 | 12 |
| 72 | 19 |
| 73 | 18 |
| 74 | 14 |
| 75 | 12 |
| 76 | 2.4 |
| 77 | 7.1 |
| 78 | 5.3 |
| 79 | 4.6 |
| 80 | 7.2 |
| 81 | 4.9 |
| 82 | 3.1 |
| 83 | 1.5 |
| 84 | 2.8 |
| 87 | 6.9 |
| 88 | 45 |
| 89 | 51 |
| 93 | 2.7 |
| 94 | 19 |
| 95 | 1.8 |
| 96 | 4.7 |
| 98 | 2.0 |
| 99 | 1.5 |
| 100 | 2.1 |
| 101 | 16 |
| 102 | 37 |
| 105 | 9.9 |
| 106 | 88 |
| 107 | 4.5 |
| 108 | 2.6 |
| 110 | 2.7 |
| 111 | 6.2 |
| 112 | 98 |
| 113 | 3.0 |
| 114 | 5.3 |
| 115 | 5.7 |
| 116 | 5.8 |
| 117 | 1.6 |
| 118 | 9.1 |
| 119 | 4.6 |
| 121 | 14 |
| 122 | 8.8 |
| 123 | 7.4 |
| 126 | 14 |
| 128 | 18 |
| 130 | 14 |

EXAMPLE 2 a) Preparation of a Physical Mixture

A 100/300 (w/w) mixture of Compound A (1kg) and hydroxypropyl methylcellulose 2910 5 mPa.s or HPMC 2910 5 mPa.s (3kg) were both sieved and mixed in a planetary mixer until the mixture was homogenous.

b) Preparing the Melt Extrudate

The physical mixture was fed into a twin screw melt extruder of the type APV-Baker MP19 PH 25:1 having the following operating parameters: temperature of the first compartment T1 was 50–80° C., T2=180–200° C., T3=200–220° C., T4=200–220° C., T5 =200–220° C., the twin screw had a rate of 50–500 revolutions/min and was extruded during 120 minutes. The extrudate was brought in a hammer mill of type Fitzmill, the mesh of the sieve was 850 μm and revolving speed was 4760 revolutions per minute. The milled extrudate was again brought in a hammer mill, this time with a sieve of mesh 500 μm and a revolving speed of 4760 revolutions per minute.

c) Preparation of a Tabletting Mixture

Spray-dried lactose monohydrate: microcrystalline cellulose (75:25) (226 g, 30.38% (w/w)), Crospovidone (62.8 g, 8.44% (w/w)), Aerosil (colloidal silicon dioxide) (2 g, 0.27% (w/w)) were sieved and mixed together with the milled extrudate (400 g, 53.77% (w/w)) using a planetary mixer until a homogenous mixture was obtained (10 minutes). This was then blended with Sterotex (6.8 g, 0.91% (w/w)), talc (20.6 g, 2.77%) and magnesium stearate (1.8 g, 0.23%) in a planetary mixer until a homogenous mixture was obtained (3 minutes).

d) Tabletting

Using the mixture obtained in c) 1000 oval biconvex half-scored tablets of 720 mg were prepared on an Excenterpress Courtoy 27.

e) Film-Coating

The tablets obtained in d) were film-coated using a suspension comprising by weight: HPMC 2910 5 mPa.s (8.6%), propylene glycol (2.1%) talc (1.7%), and titanium dioxide (2.6%) in demineralised water (85%). HPMC 2910 5 mPa.s was added to the two thirds of the purified water and mixed until completely dispersed. The solution was left to stand until clear. Propylene glycol was added and the solution was mixed until uniform. Talc and titanium dioxide were added to the remaining third of the purified water and homogenized until uniform. The solution and the suspension were then mixed together. The tablets obtained in d) were placed in a coating pan and the pigmented coating suspension was sprayed onto the cores. Average tablet weight was 744 mg.

f) Packing

The coated tablets were packed into polyvinyl/aluminium foil blister packs, which in turn were packed into cardboard cartons.

g) Dissolution Properties

In-vitro dissolutions studies were performed on the 100 mg tablet formulation. The medium was 900 ml 0.1 N HCl at 37° C. in Apparatus 2 (USP 23, <711> Dissolution, pp. 1791–1793) (paddle, 50 rpm). The concentration of the active ingredient Compound A dissolved in the test medium was determined by removing a 3 ml sample at the indicated time, measuring its absorbance at 254 nm and calculating the concentration therefrom. The following results were obtained:

| Time (min) | Calculated concentration (% w/w) of the active dose | | | | | | |
|---|---|---|---|---|---|---|---|
| | sample 1 | sample 2 | sample 3 | sample 4 | sample 5 | sample 6 | average |
| 0 | 0.6 | 0.0 | −0.1 | 0.0 | 0.0 | 0.1 | 0.1 |
| 10 | 54.7 | 81.7 | 77.9 | 41.8 | 71.3 | 54.6 | 63.7 |
| 20 | 77.2 | 91.4 | 91.1 | 78.6 | 90.3 | 75.7 | 84.0 |
| 30 | 84.4 | 93.4 | 94.0 | 87.9 | 93.7 | 83.8 | 89.5 |
| 45 | 89.8 | 95.0 | 96.1 | 94.2 | 96.4 | 91.5 | 93.8 |
| 60 | 92.7 | 95.7 | 96.9 | 96.8 | 97.8 | 95.7 | 95.9 |

EXAMPLE 3

Comparative Bioavailability of the Melt Extrusion Tablet Versus Oral Solution, and the Influence of Food In an open, randomised, parallel group, three-way crossover trial, the oral bioavailability of the melt extrusion tablet comprising 100 mg of Compound A was compared to that of an oral solution. Three groups of six healthy male volunteers took a single oral dose of 100 mg of Compound A in the tablet formulation under fasting conditions and directly after a standard breakfast, and as an oral solution under fasting conditions. The pharmacokinetics were assessed for the unchanged drug only and are summarized in the table hereunder.

| Parameter | tablet fasting | tablet breakfast | solution fasting |
|---|---|---|---|
| $t_{max}$, h | 3.0 ± 0.6 | 3.6 ± 1.5 | 1.3 ± 0.4 |
| $C_{max}$, ng/ml | 37.9 ± 14.9 | 38.9 ± 15.1 | 67.50 ± 26.1 |
| $F_{rel}\ C_{max}$, % | 59.6 ± 17.7 | 68.7 ± 43.1 | 100 |
| $t_{1/2term}$, h | 3.5 ± 0.6 | 3.4 ± 0.4 | 4.0 ± 0.7 |
| $AUC_\infty$, ng · h/ml | 225 ± 82 | 252 ± 46 | 318 ± 123 |
| $F_{rel}\ AUC_\infty$, % | 74.7 ± 19.3 | 88.8 ± 32.9 | 100 |

EXAMPLE 4 a) Milled Melt Extrudate

The extrudate was brought into a hammer mill of the type Fitzmill and sieved to isolate particles having a size in the range of 600 to 850 mm (30 to 20 mesh ASTM E11-70).

b) Seal-coating Spraying Solution

A vessel was charged with methylene chloride (252 g) and polyethylene glycol 20000 (Macrogol 20000) (28 g) while stirring. The mixture was stirred until homogeneous.

c) Coating Process

A fluidized-bed granulator (Uniglatt) equipped with a 1 inch Wurster (bottom spray) insert was loaded with milled melt extrudate (700 g). The particles were warmed with dry air of 45°–55° C. The fluidizing air volume was controlled by opening the exhaust air valve to approximately 45% of its maximum. The previously prepared seal-coating spraying solution was then sprayed on the particles moving in the apparatus at a delivery rate of about 20 g.min-1 and at an atomizing air pressure of about 1.7 bar (0.17 MPa). When the spraying process was completed, the coated particles were dried by further supplying dry air of 50°–55° C. for about 10 minutes. The coated particles were then allowed to cool in the apparatus by supplying dry air of 20–25° C. for about 5 minutes. The apparatus was emptied and the coated particles (718 g) were stored in suitable containers.

d) Capsule Filling

The coated particles were filled into hard-gelatin capsules (410 mg coated particles equivalent to 100 mg active ingredient in size number 0) using standard automatic capsule filling machines (e.g. Model Bosch GKF130). Capsule filling speed was about 8000 capsules per hour. Using the process parameters described above, hard-gelatin capsules containing 100 mg Compound A were obtained which met all the requirements, in particular the dissolution specifications.

e) Dissolution Properties

In-vitro dissolution studies were performed on the 100 mg capsule formulation. The medium was 900 ml 0.1 N HCl at 37° C. in Apparatus 2 (USP 23, <711> Dissolution, pp. 1791–1793) (paddle, 75 rpm). The concentration of the active ingredient Compound A dissolved in the test medium was determined by removing a 3 ml sample at the indicated time, measuring its absorbance at 253 nm and calculating the concentration therefrom. The following results were obtained:

| Time (min) | Calculated concentration (% w/w) of the active dose | | | | | | |
|---|---|---|---|---|---|---|---|
| | sample 1 | sample 2 | sample 3 | sample 4 | sample 5 | sample 6 | average |
| 0 | 0.0 | 0.0 | 0.0 | 0.0 | 0.0 | 0.0 | 0.0 |
| 10 | 39.4 | 35.5 | 31.3 | 35.6 | 40.0 | 41.8 | 37.3 |
| 20 | 59.1 | 62.0 | 59.1 | 66.7 | 71.1 | 79.5 | 66.3 |
| 30 | 75.0 | 73.0 | 72.3 | 79.0 | 82.1 | 89.6 | 78.5 |
| 45 | 86.4 | 83.7 | 83.2 | 86.9 | 89.4 | 95.0 | 87.4 |
| 60 | 92.5 | 89.6 | 90.6 | 92.5 | 94.4 | 96.0 | 92.6 |

What is claimed is:
1. A particle consisting of a solid dispersion comprising
(a) a lipid lowering agent of formula

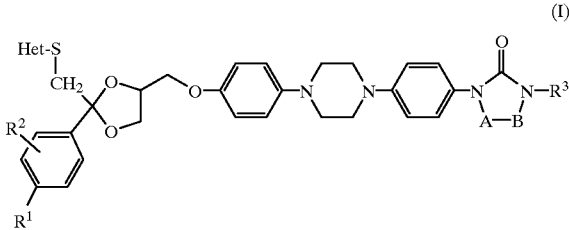

an N-oxide, a stereochemically isomeric form, a mixture of two or more such forms, or a pharmaceutically acceptable acid addition salt thereof, wherein A and B taken together form a bivalent radical of formula:

| | |
|---|---|
| —N=CH— | (a), |
| —CH=N— | (b), |
| —CH$_2$—CH$_2$— | (c), |
| —CH=CH— | (d), |
| —C(=O)—CH$_2$— | (e), |
| —CH$_2$—C(=O)— | (f), | in the bivalent radicals of formula (a) and (b) the hydrogen atom may be replaced by $C_{1-6}$alkyl; in the bivalent radicals of formula (c), (d), (e), (f), one or two hydrogen atoms may be replaced by $C_{1-6}$alkyl;

$R^1$ is hydrogen, $C_{1-6}$alkyl or halo;

$R^2$ is hydrogen or halo;

$R^3$ is hydrogen; $C_{1-8}$alkyl; $C_{3-6}$cycloalkyl; or $C_{1-8}$alkyl substituted with hydroxy, oxo, $C_{3-6}$cycloalkyl or aryl;

Het is a heterocycle selected from the group consisting of pyridine; pyridine substituted with one or two substituents selected from $C_{1-6}$alkyl, hydroxy, $C_{1-6}$alkyloxy, trihalomethyl, amino, mono- or di($C_{1-6}$alkyl)amino or aryl; pyrimidine; pyrimidine substituted with one or two substituents selected from $C_{1-6}$alkyl, hydroxy, $C_{1-6}$alkyloxy, trihalomethyl, amino, mono- or di($C_{1-6}$alkyl)-amino or aryl; tetrazole; tetrazole substituted with $C_{1-6}$alkyl or aryl; triazole; triazole substituted with one or two substituents selected from $C_{1-6}$alkyl, hydroxy, $C_{1-6}$alkyloxy, trihalomethyl, amino, mono- or di($C_{1-6}$alkyl)-amino; thiadiazole; thiadiazole substituted with one or two substituents selected from $C_{1-6}$alkyl, hydroxy, $C_{1-6}$alkyloxy, trihalomethyl, amino, mono- or di($C_{1-6}$alkyl)amino; oxadiazole substituted with one or two substituents selected from $C_{1-6}$alkyl, hydroxy, $C_{1-6}$alkyloxy, trihalomethyl, amino, mono- or di($C_{1-6}$alkyl)amino; imidazole; imidazole substituted with one or two substituents selected from $C_{1-6}$alkyl, hydroxy, $C_{1-6}$alkyloxy, trihalomethyl, amino, mono- or di($C_{1-6}$alkyl)amino; thiazole; thiazole substituted with one or two substituents selected from $C_{1-6}$alkyl, hydroxy, $C_{1-6}$alkyloxy, trihalomethyl, amino, mono- or di($C_{1-6}$alkyl)amino; oxazole; oxazole substituted with one or two substituents selected from $C_{1-6}$alkyl, hydroxy, $C_{1-6}$alkyloxy, trihalomethyl, amino, mono- or di($C_{1-6}$alkyl)amino;

aryl is phenyl or phenyl substituted with $C_{1-6}$alkyl or halo; and one or more pharmaceutically acceptable water-soluble polymers.

2. A particle according to claim 1 having a particle size of less than 850 µm.

3. A particle according to claim 1 wherein the lipid lowering agent is in a non-crystalline phase.

4. A particle according to claim 3 wherein the solid dispersion is in the form of a solid solution comprising (a) and (b), or in the form of a dispersion wherein amorphous or microcrystalline (a) or amorphous or microcrystalline (b) is dispersed more or less evenly in a solid solution comprising (a) and (b).

5. A particle according to the claim 4 wherein the water-soluble polymer is a polymer that has an apparent viscosity of 1 to 100 mPa.s when dissolved in a 2% aqueous solution at 20° C. solution.

6. A particle according to claim 5 wherein the water-soluble polymer is selected from the group consisting of
alkylcelluloses,
hydroxyalkylcelluloses,
hydroxyalkyl alkylcelluloses,
carboxyalkylcelluloses,
alkali metal salts of carboxyalkylcelluloses,
carboxyalkylalkylcelluloses,
carboxyalkylcellulose esters,
starches,
pectines,
chitin derivates,
polysaccharides,
polyacrylic acids and the salts thereof,
polymethacrylic acids and the salts thereof,
methacrylate copolymers,
polyvinylalcohol,
polyvinylpyrrolidone,
copolymers of polyvinylpyrrolidone with vinyl acetate and
polyalkylene oxides.

7. A particle according to claim 6 wherein the water-soluble polymer is hydroxypropyl methylcellulose HPMC 2910 5 mPa.s.

8. A particle according to claim 7 wherein the weight-by-weight ratio of (a):(b) is in the range of 1:1 to 1:35.

9. A particle according to claim 1 obtainable by melt-extrusion of the components and grinding, and optionally sieving.

10. A particle according to claim 1 consisting of a solid solution comprising one part by weight of lipid lowering agent and from one to three parts by weight of hydroxypropyl methylcellulose HPMC 2910 5 mPa.s, obtainable by blending said components, extruding the blend at a temperature in the range of 120° C.–300° C., grinding the extrudate, and optionally sieving the thus obtained particles.

11. A particle according to the claim 1 further comprising one or more pharmaceutically acceptable excipients.

12. A particle according to claim 1, wherein the lipid lowering agent is cis-4-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-2-(1-methyl-propyl)-3H-1,2,4-triazol-3-one.

13. A pharmaceutical dosage form comprising a therapeutically effective amount of particles as claimed in claim 1.

14. A dosage form according to claim 13 adapted for oral administration shaped as a tablet.

15. A dosage form according to claim 13 for immediate release of a lipid lowering agent upon oral ingestion wherein said particles are homogeneously distributed throughout a mixture of a diluent and a disintegrant.

16. A dosage form according to claim 14 surrounded by a film-coat comprising a film-forming polymer, a plasticizer and optionally a pigment.

17. A dosage form according to claim 15 wherein the diluent is a spray-dried mixture of lactose monohydrate and microcrystalline cellulose (75:25), and the disintegrant is crospovidone or croscarmellose.

18. A dosage form according to claim 17 wherein the weight of said particles is at least 40% of the total weight of the dosage form.

19. A dosage form according to claim 13 comprising by weight based on the total weight of the dosage form:

| | |
|---|---|
| 13.44% | Compound A (100 mg) |
| 40.32% | HPMC 2910 5 mPa.s (300 mg) |
| 30.38% | spray-dried lactose monohydrate:microcrystalline cellulose (75:25) mixture (226 mg) |
| 8.44% | crospolyvidone (62.8 mg) |
| 2.77% | talc (20.6 mg) |
| 0.91% | hydrogenated vegetable oil Type I (6.8 mg) |
| 0.27% | colloidal anhydrous silica (2 mg) |
| 0.23% | magnesium stearate (1.8 mg), yielding |
| 96.77% | tablet core (720 mg), and |
| 1.84% | HPMC 2910 5 mPa.s (13.7 mg) |
| 0.46% | propylene glycol (3.282 µl) (3.4 mg) |
| 0.37% | talc (2.76 mg) |
| 0.56% | titanium dioxide (4.14 mg), yielding |
| 3.23% | film-coat (24 mg), together forming |
| 100% | film-coated tablet (744 mg). |

20. A dosage form according to claim 13 adapted for oral administration shaped as a capsule.

21. A dosage form according to claim 20 wherein the particles are covered with a seal coat polymer layer.

22. A dosage form according to claim 21 wherein the seal coat poymer is polyethylene glycol 20000.

23. A dosage form according to claim 22 from which at least 40% of the available lipid lowering agent dissolves within 60 minutes when a dosage form equivalent to 100 mg lipid lowering agent is tested as set forth in USP test <711> in a USP-2 dissolution apparatusunder conditions at least as stringent as the following: 900 ml 0.1 N HCl, pH 6.0, 37° C. with paddles turning at 50 rpm.

24. A process of preparing particles as claimed in claim 12 characterized by blending the components, extruding said blend at a temperature in the range of 120–300° C., grinding the extrudate, and optionally sieving the particles.

25. A solid dispersion obtainable by melt-extrusion of
(a) a lipid lowering agent of formula (I) as described in claim 1, a stereoisomer or a mixture of two or more stereoisomers, and
(b) one or more pharmaceutically acceptable water-soluble polymers.

26. A process of preparing a pharmaceutical dosage form as claimed in characterized by blending a therapeutically effective amount of particles as claimed in claim 11 with pharmaceutically acceptable excipients and compressing said blend into tablets.

27. Particles according to claim 12 for use in preparing a pharmaceutical dosage form for oral administration to a mammal suffering from hyperlipidemia, obesitas or atherosclerosis, wherein a single such dosage form can be administered once daily to said mammal.

28. Particles according to claim 12 for use in preparing a pharmaceutical dosage form for oral administration to a mammal suffering from hyperlipidemia, obesitas or atherosclerosis, wherein said dosage form can be administered at any time of the day independently of the food taken in by said mammal.

29. A method for treating a mammal suffering from hyperlipidemia, obesitas or artherosclerosis comprising orally administering to said mammal a pharmaceutical dosage form comprising a particle according to claim 1, wherein a single such dosage form can be administered once daily to said mammal.

30. A method for treating a mammal suffering from hyperlipidemia, obesitas or atherosclerosis, comprising orally administering a pharmaceutical dosage form comprising a particle according to claim 1, wherein said dosage form can be administered at any time of the day independently of the food taken in by said mammal.

31. A pharmaceutical package suitable for commercial sale comprising a container, an oral dosage form of lipid lowering agent as claimed in claim 23 and associated with said package written matter non-limited as to whether the dosage form can be taken with or without food.

32. A particle according to claim 1, wherein the lipid lowering agent is (−)-[2S-[2alpha,4alpha(S*)]]-4-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-2-(1-methylpropyl)-3H-1,2,4-triazol-3-one.

* * * * *